United States Patent
Wendel et al.

(10) Patent No.: US 7,240,790 B2
(45) Date of Patent: Jul. 10, 2007

(54) MULTIPLE-POUCH PACKAGE FOR A SUPPORT IMPREGNATED WITH A PRODUCT FOR APPLICATION ON THE SKIN AND FOR MEANS PROTECTING THE TREATED SKIN ZONE

(75) Inventors: Serge Wendel, Ricquewihr (FR); Wilton Dos Santos, Strasbourg (FR)

(73) Assignee: Compagnie Europeenne de Compresse Et de Pansements-Cecep Societe Par Actions Simplifiee, Annonay (FR)

( * ) Notice: Subject to any disclaimer, the term of this patent is extended or adjusted under 35 U.S.C. 154(b) by 756 days.

(21) Appl. No.: 10/311,342

(22) PCT Filed: Jul. 6, 2001

(86) PCT No.: PCT/EP01/07773

§ 371 (c)(1),
(2), (4) Date: Jan. 3, 2003

(87) PCT Pub. No.: WO02/02042

PCT Pub. Date: Jan. 10, 2002

(65) Prior Publication Data

US 2003/0194426 A1    Oct. 16, 2003

(30) Foreign Application Priority Data

Jul. 6, 2000    (FR) .................... 00 08869

(51) Int. Cl.
*B65D 81/24*    (2006.01)
*A61B 19/02*    (2006.01)
*A61M 35/00*    (2006.01)
*A61F 13/02*    (2006.01)

(52) U.S. Cl. ............... 206/210; 206/440; 206/812; 604/289; 604/307

(58) Field of Classification Search ............... 206/438, 206/440, 205, 207, 210, 223, 484, 494, 812, 206/441; 604/289–290, 304–308

See application file for complete search history.

(56) References Cited

U.S. PATENT DOCUMENTS

| 4,304,333 A |   | 12/1981 | Kozlow et al. |
| 4,332,319 A | * | 6/1982 | Hurwood ............... 206/210 |
| 4,360,020 A |   | 11/1982 | Hitchcock, Jr. et al. |
| 4,519,795 A | * | 5/1985 | Hitchcock et al. ......... 604/289 |
| 4,557,381 A | * | 12/1985 | Whitney ............... 206/440 |

(Continued)

FOREIGN PATENT DOCUMENTS

| FR | 1.408.584 | 12/1965 |
| WO | WO 85/03275 | 8/1985 |

(Continued)

*Primary Examiner*—Bryon P. Gehman
(74) *Attorney, Agent, or Firm*—Westerman, Hattori, Daniels & Adrian, LLP.

(57) ABSTRACT

A multiple-pouch package includes a first pouch wherein is fixed a support impregnated with a substance to be applied on the skin and at least a pouch containing a protection for the skin zone treated with the applied substance. The protection can consist of an adhesive plaster, a bandage, a compress or a dressing. Rupture-proof devices are provided to prevent the two walls of a common pouch to be entirely separated when it is opened. Opening facilitators are provided to facilitate the opening of the different pouches. The multiple-pouch package can be produced by fixing the different single pouches one to the other or by folding on itself one strip to form the various pouches.

19 Claims, 2 Drawing Sheets

U.S. PATENT DOCUMENTS

Figure 1:
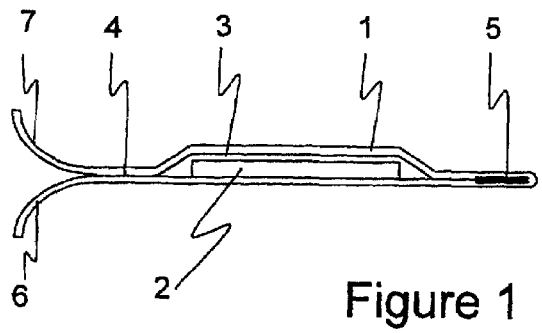

| | | | |
|---|---|---|---|
| 4,796,751 A | * | 1/1989 | Madkour .................... 206/223 |
| 4,915,102 A | * | 4/1990 | Kwiatek et al. ............ 604/307 |
| 4,946,033 A | * | 8/1990 | Conner ....................... 206/223 |
| 5,242,433 A | * | 9/1993 | Smith et al. ................ 604/289 |
| 5,254,109 A | * | 10/1993 | Smith et al. ................ 604/289 |
| 5,261,531 A | * | 11/1993 | Nieves ....................... 206/440 |
| 5,368,581 A | * | 11/1994 | Smith et al. ................ 604/290 |
| 5,417,674 A | * | 5/1995 | Smith et al. ................ 604/289 |
| 5,460,620 A | * | 10/1995 | Smith et al. ................ 604/290 |
| 5,487,932 A | | 1/1996 | Dunshee |
| 5,562,642 A | * | 10/1996 | Smith et al. ................ 604/289 |

* cited by examiner

MULTIPLE-POUCH PACKAGE FOR A SUPPORT IMPREGNATED WITH A PRODUCT FOR APPLICATION ON THE SKIN AND FOR MEANS PROTECTING THE TREATED SKIN ZONE

This invention concerns a package for a support impregnated with a product for application to the skin, comprising a first pouch constituted essentially of two walls fixed to each other by appropriate fixation means that make it possible, at the time of utilization, to at least partially separate said walls, said pouch being intended to contain a support impregnated with the product to be applied, the impregnated support being fixed by appropriate means to the internal surface of at least one of the walls of the first pouch.

It is common in pharmaceutics, in cosmetics or in perfumery to utilize supports impregnated with a product for application to the skin presented in pouches for single use. The pouch is opened and the support impregnated with the product to be applied is taken out in order then to be affixed to the chosen part of the skin. These single-use pouches are often used as promotional items, while traveling or also in the field of pharmaceutics, when the use of a single dose is preferred, for example when the sterility of the product to be applied must be ensured.

Such pouches are described in particular in documents WO 98/56 568 or EP 0 953 303. A major disadvantage of these pouches lies in the fact that it is necessary to grasp the impregnated support in order to apply the product to the chosen part of the skin. The product to be applied is then deposited not only on the chosen part of the skin but also on the fingers handling the impregnated support. This can prove to be very bothersome, for example because of the color of the applied product, for example eosin in pharmaceutics, which necessitates careful washing of the hands after application. Moreover, it is common that this operation takes place under uncertain hygienic conditions. This is in particular the case with disinfectant or cicatrizant wipes utilized during an outing in the absence of a water source to wash the hands beforehand. If the product to be applied is presented in an envelope ensuring its sterility during storage, this sterility is no longer ensured and the impregnated support is contaminated by the fingers at the risk of then contaminating the wound and causing an infection.

To remedy this disadvantage, pouches have been proposed wherein the impregnated support is fixed to at least one of the walls of the pouch. Such pouches are known from U.S. Pat. No. 5,487,932 A, U.S. Pat. No. 4,360,020 A, WO 85 03 275 A and FR 1 408 584 A.

Moreover, U.S. Pat. No. 4,360,020 presents a double-pouch package, each pouch possessing an impregnated support.

In the field of first aid, however, it is sometimes necessary to have not only a support impregnated with a solution for local application, such as a disinfectant or a cicatrizant, but also something to protect the zone thus treated. It is therefore necessary to remember to arrange together or to take out, on the one hand, something to treat the wound and, on the other hand, something to protect it. During outings or while traveling, for example, the risk of misplacing one or the other element in a bag is great. Moreover, utilization of several packages increases the quantity of elements to be discarded, at the risk of forgetting some of them by the side of the road.

Therefore, an object of the invention is to develop a package of the kind described in the preamble that makes it possible to easily find the different elements necessary for the treatment and protection of a skin zone.

This objective is attained by a package of the kind presented previously and that comprises at least an additional pouch constituted essentially of two walls fixed to each other by appropriate means of fixation that make it possible, at the time of utilization, to at least partially separate said walls, this pouch being intended for receiving the means for protecting the treated skin zone. Thus, the same package comprises in two different pouches, on the one hand, an impregnated support and, on the other hand, means for protecting the treated zone. The means of protection may be constituted by a bandage, a compress, a bandaid or a dressing.

In order to facilitate the application of the product, it is preferable that the wall or each wall of the first pouch whereon is fixed the impregnated support should be constructed of a flexible material. It will be easier to apply the product in recessed or projecting zones of the skin.

In order to optimize the form and the storage of packages conforming to the invention, it is planned to superpose at least two pouches on each other in such a way that two successive pouches are connected by a common wall. This common wall can be formed by fixing, through appropriate means, the exterior surfaces of the walls of two pouches, that is to say by fixing two individual pouches one on the other. This common wall can also be obtained by utilizing the two surfaces of a single wall in such a way as to obtain on one side the internal surface of the first pouch and on the other side the internal surface of the next pouch.

These additional pouches are provided principally in order to receive, according to the intended purpose of the package, a bandage, a compress, a bandaid, a dressing or an additional support impregnated with the same product or with another product, the compress or the additional impregnated support being capable of being fixed on at least one of the walls of said pouch. It is thus possible to combine a disinfectant and/or a cicatrizant with a dressing.

Means can be provided, in pouches intended most particularly for sterile pharmaceutical products, to guarantee the sterility of the content of the product during storage. For example, a material that is suited to guarantee the sterility of the product is chosen to manufacture the walls of these pouches, such as, for example, layers of laminate or laminate complex. The fixation of the walls will then be ensured, for example, by bonding, gluing or heat sealing.

In order to facilitate the opening of pouches, it is preferable that the means of fixation of the walls of each pouch makes possible a separation by peeling of said walls at the time of the opening of the pouch under consideration.

It is consistent with the invention to provide for anti-breakup means at least on the first pouch to prevent, at the time of the opening of the pouch under consideration, the walls forming it from separating totally. The anti-breakup means of pouches containing an impregnated support can be constituted in particular by the fixation of said impregnated support to the two walls of the pouch containing it. Thus, when the impregnated support, folded in two, is fixed to the two walls of the pouch, it prevents, by its own strength, the total separation of the walls. Another solution consists in fixing the two walls over a certain section by a mode of fixation much stronger than over the rest of the pouch. If the pouch is formed by two rectangular films fixed to each other, for example by bonding, three of the bonds will open easily by simple peeling while the fourth bond will resist the tearing, for example thanks to the impregnated support fixed on the two walls or to another type of bond that is stronger.

In the latter case, this stronger bond can be used as a handle facilitating the handling of the impregnated support. At the time of utilization, the first pouch is opened, the wall or walls upon which the impregnated support is fixed is grasped by the user in order to apply the product. When the application is finished, the free wall of the first pouch is folded back to cover the impregnated support and the second pouch is opened in order to gain access to its contents. By equipping the two pouches with such anti-breakup means, the number of pieces to be discarded after utilization is reduced, thus avoiding the misplacement or blowing-away of pieces of packaging that could pollute the environment.

In order to facilitate the opening of each pouch, they may comprise opening means. Tongues, forming an extension of the walls of the pouch beyond one of the bonds, for example, are capable of being used as opening means.

When several superposed pouches comprise such anti-breakup and/or opening means, it is preferable that the anti-breakup means and/or the opening means of one pouch be placed on the wall common to the two pouches, staggered or on the opposite in relation to, respectively, the anti-breakup means and/or the opening means of the next pouch. By placing these opening means staggered or opposite with respect to each other, opening one pouch inadvertently at the time of the opening of another pouch is avoided.

Figure 2:
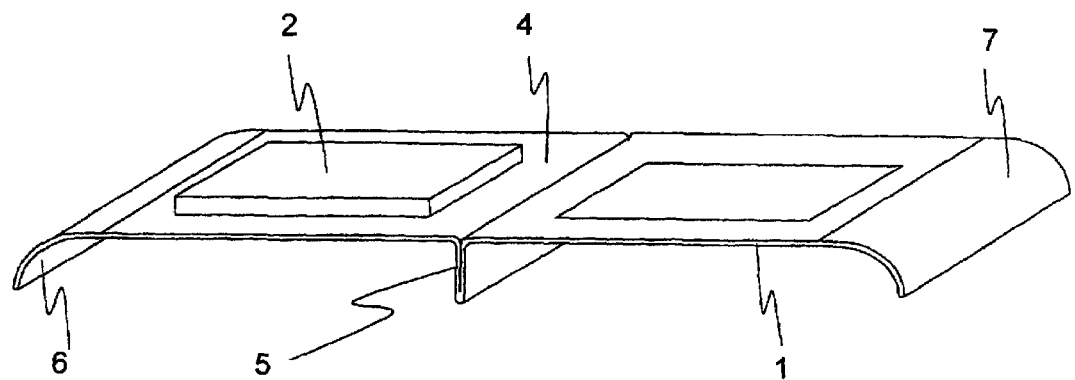
Figure 3:
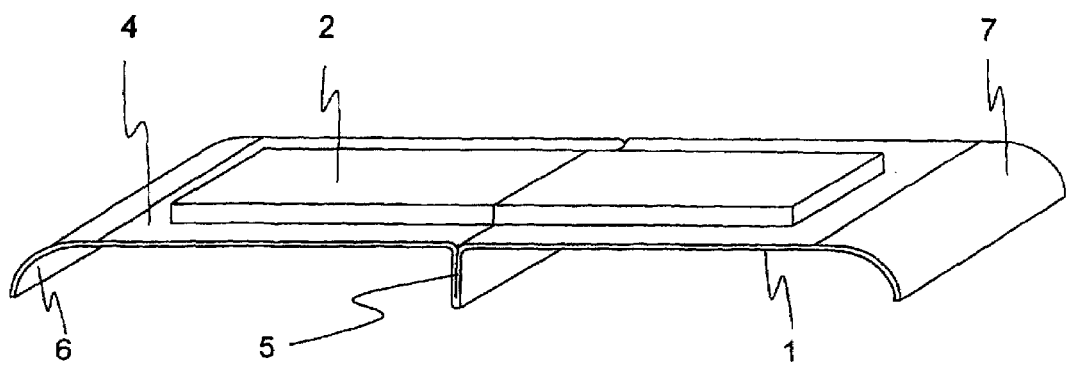
Figure 4:
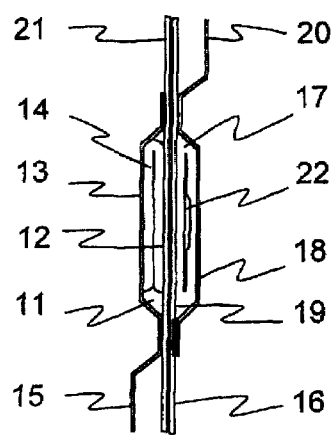
Figure 5:
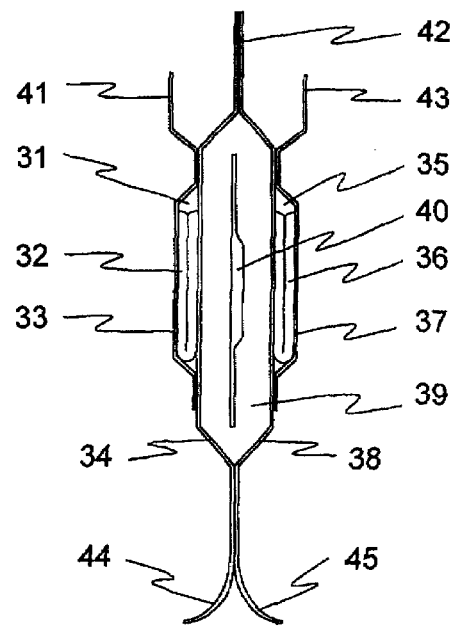
Figure 6:
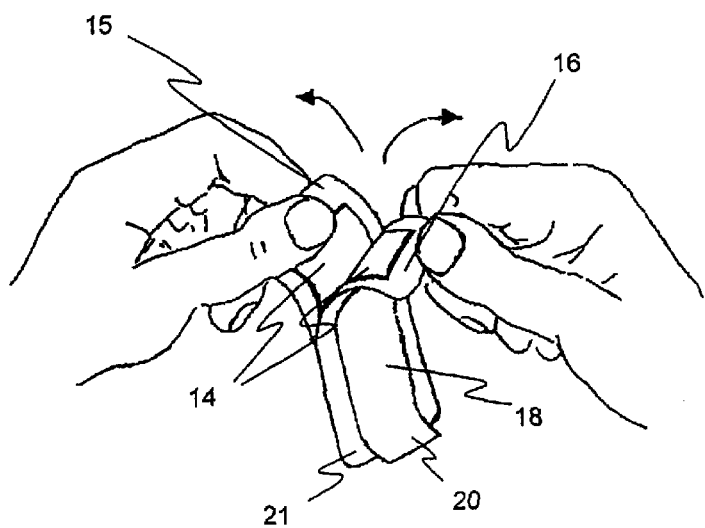

Several examples of embodiments of the invention are presented below by means of the following figures:

FIG. 1. First pouch containing an impregnated support fixed to a single wall of the pouch;

FIG. 2. The first pouch of FIG. 1 after opening;

FIG. 3. First pouch, opened, containing an impregnated support fixed to the two walls of the pouch;

FIG. 4. Package with two pouches, closed, containing an impregnated support fixed to the two walls of the first pouch and a dressing in the second pouch;

FIG. 5. Package with three pouches, closed, containing two impregnated supports and a dressing;

FIG. 6. User opening a package with two pouches.

The package according to the invention comprises a first pouch (3, 11, 31) in which an impregnated support (2, 14, 32) is fixed, and at least a second pouch (17, 39) containing means for protecting the treated skin zone, such as a bandaid, a bandage, a compress or a dressing (22, 40).

The pouches may be constituted in different ways.

In a first embodiment, the pouch (3) is composed of a flexible strip (1) made of laminate or laminate complex. The strip (1) is folded in the middle in such a way as to enclose the impregnated support (2) or the means for protecting the wound in a sort of pouch (3). The pouch (3) is closed on its edges by fixing the two half-strips on each other by bonding, gluing or thermosealing on the periphery (4) of the strip (1). The two half-strips then form the walls of the pouch (3).

In a second embodiment, the pouch (11, 17, 31, 35, 39) is created by utilizing two strips (12, 13, 18, 19, 33, 34, 37, 38) fixed to each other over the entire periphery.

The impregnated support (2, 14, 32) is fixed in the first pouch (3, 11, 31) by, for example, bonding. The impregnated support (2, 14, 32) may be manufactured of a synthetic or semi-synthetic material. The material of the impregnated support (2, 14, 32) is chosen for its capacity to absorb the product to be applied. The impregnated support (2, 14, 32) may be fixed either on a single wall of the pouch as shown in FIGS. 1 and 2, or on the two walls as shown in FIGS. 3, 4 and 5.

In order to avoid the proliferation of pieces to be discarded at the time of use, it is preferable that the different pouches (3, 11, 17, 31, 35, 39) be equipped with anti-breakup means (5) that prevent the two walls of a pouch from becoming entirely separated from each other. Thus, in the example shown in FIG. 2, the free wall remains linked to the package by a stronger fixation (marked in bold in FIG. 1), so that after use there is only one piece to be discarded. Moreover, this wall may be folded back over the impregnated support in order to avoid inadvertently applying the remainder of the product to be applied after use. In the examples of FIGS. 3, 4 and 5, these anti-breakup means are constituted by the impregnated support (2, 14, 32) itself, which is fixed in one piece on the two walls.

Moreover, by fixing the impregnated support (2), not in the area of the fold of the strip (1), but at a certain distance from it, and by fixing the two half-strips to each other by, for example, bonding on that portion located beyond the fold of the impregnated support, a sort of handle (5) is formed that facilitates the handling of the impregnated support (2).

In order to facilitate the opening of pouches, it is possible to form two tongues (6, 7, 15, 16, 20, 21, 41, 42, 43, 44, 45) on either side of the opening bond, preferably opposite to the anti-breakup means. The rectangular general form is not obligatory. For example, a circular form can be chosen, in particular when the impregnated support is fixed to only one wall of the pouch.

The package according to the invention may be obtained by superposing at least two single pouches of the type shown in FIGS. 1 to 3.

In order to do this, it is possible to either fix single pouches to each other, or to fold one strip several times on itself like an accordion in order to form successive pouches whose peripheral edges are, for example, bonded.

The example of FIG. 4 comprises a first pouch (11) formed by two strips (12, 13) bonded to each other at their peripheral edges, thus forming the two principal walls of the first pouch (11). An impregnated support (14) is fixed to the two walls (12, 13) of the first pouch (11). When the user pulls, as shown in FIG. 6, on the tongues (15, 16) formed by the ends of the strips (12, 13), he opens the pouch by peeling. By folding back the exterior strip (13), the impregnated support (14) is unfolded and the product may be applied. The impregnated support (14) is fixed to the walls (12, 13) of the pouch (11) in such a way that the walls cannot separate. If the impregnated support (14) were fixed to only one of the walls, for example the central wall (12), it would be possible to fix the exterior wall (13) to the central wall (12) at one of its peripheral edges by a stronger bond, in order to avoid the separation of the exterior wall (13) from the rest of the package. This strong bond would then fulfill the function of anti-breakup means.

A second pouch (17), formed by two strips (18, 19) bonded together, is fixed on the wall (12) of the first pouch (11). Means for facilitating the opening of this second pouch (17) are also provided, in the form of tongues (20, 21) constituted by the ends of the strips (18, 19) forming the second pouch (17). The fixation of the exterior strip (18) to the central strip (19) will be done in such a way as to make possible an at least partial separation of the walls by peeling. The fixation located opposite to the tongues (20, 21) will preferably be stronger, in order to avoid the complete separation of the wall (18) from the rest of the package. The strips (12, 19) form a wall common to the two pouches.

The second pouch contains means for protecting the treated skin zone, for example a bandaid, a dressing (22), a compress or a bandage.

A pouch of this kind can also be obtained by folding the same strip two times like an accordion or by fixing two exterior strips to a central strip forming the common wall.

The means for facilitating the opening (15, 16, 20, 21) of the two pouches (11, 17) will be positioned opposite each other, thus avoiding the opening of one pouch in place of the other.

FIG. 5 shows another packaging example comprising three pouches. The first pouch (31) contains an impregnated support (32) fixed to two walls (33, 34), an additional pouch (35) contains a second impregnated support (36) fixed to two walls (37, 38) and the second pouch (39) formed by the external surfaces of the walls (34, 38) of the two other pouches contains the means for protecting the treated skin zone, for example a bandaid, a dressing (40), a bandage or a compress. This package may be used as a first-aid kit. The user opens the first pouch (31) by separating the tongues (41, 42) in order to unfold the first impregnated support (32) of, for example, disinfectant. Once the wound is disinfected, the user folds back the wall (33) and opens the additional pouch (35) to gain access to the second impregnated support (36) of, for example, cicatrizant. In order to facilitate the opening of the additional pouch (35), this pouch also presents two tongues (42, 43). Finally, the dressing (40) contained in the second pouch (39) may be liberated by opening this latter pouch by means of the tongues (44, 45). Once again, it is preferable that this second pouch be equipped with anti-breakup means, for example by bonding its two walls more strongly on the side opposite to the tongues (44, 45). After the operation is finished, all the components of the package are integral with each other, which results in not more than one piece to be discarded. Therefore there is no risk of littering from the remains of the first-aid kit.

By positioning the tongues as shown in FIGS. 4, 5 and 6, the successive opening of the different pouches is facilitated, without risking the opening of one pouch in place of another.

Although the packages cited here by way of example comprise only two or three pouches, it is self-evident that this number is not limited and that it is possible to produce packages with a larger number of pouches according to the use envisaged.

It is also possible to place the anti-breakup means or the means for facilitating the opening of the successive pouches, not opposite each other, but in a staggered manner. This will be the case, for example, if a package with three pouches of triangular form is chosen. The anti-breakup means will each be positioned on an edge of the triangle and the means to facilitate opening on the opposite angle.

Instead of superposing the different pouches on each other, it is also possible to line them up. A package with two pouches may be formed, for example, from an elongated lower strip on which are fixed two upper strips of smaller dimensions in order to form two pouches side by side. These pouches can be equipped as in the examples presented previously with anti-breakup means formed, for example, by stronger fixations or by the impregnated support fixed to the two walls, as well as with means facilitating opening, for example in the form of tongues, which may be positioned staggered with respect to each other.

The composition of the strips forming the walls will depend on the use made of the pouches. Pouches containing a liquid or semi-solid product will be produced of moisture-proof materials compatible with the product contained, for example out of laminate or laminate complex of polyester/aluminum/polyethylene. As need be, the material shall ensure the sterility of the product contained in the pouch. For pouches containing bandaids, compresses, dressings or bandages, it will be possible to utilize paper strips with an acrylic varnish. The impregnated support may, for example, be produced of polyester foam. By producing multiple-pouch packages by fixation of different single pouches to each other, it is possible to utilize different materials for the different contents.

The package according to the invention therefore presents numerous advantages with respect to known packages. The principal advantage lies in the fact that the same package contains the product for application to the skin and the means for protecting the skin zone thus treated. There is therefore no risk of forgetting one or the other or of misplacing one of these elements.

Since the different elements forming the package can be kept integral with each other by the anti-breakup means, the user has, throughout the different utilization steps, only a single piece to manipulate and finally to discard.

LIST OF REFERENCES

1 Strip
2 Impregnated support
3 Pouch
4 Periphery of the pouch
5 Handle
6 Tongue
7 Tongue
11 Pouch
12 Strip
13 Strip
14 Impregnated support
15 Tongue
16 Tongue
17 Pouch
18 Strip
19 Strip
20 Tongue
21 Tongue
22 Dressing
31 Pouch
32 Impregnated support
33 Strip
34 Strip
35 Pouch
36 Impregnated support
37 Strip
38 Strip
39 Pouch
40 Dressing
41 Tongue
42 Tongue
43 Tongue
44 Tongue
45 Tongue

The invention claimed is:

1. Package for a support impregnated with a product for application to the skin, comprising:
    a first pouch comprising two walls fixed to each other so as to make it possible, at a time of use, to at least partially separate said walls of the first pouch,
    the first pouch containing the support impregnated with the product to be applied, the impregnated support being fixed to an internal surface of at least one of the walls of the first pouch, and
    at least a second pouch comprising two walls fixed to each other so as to make it possible, at the time of use, to at least partially separate said walls of the second pouch,
    the second pouch containing means for protecting a treated skin zone, the protecting means being unattached to the walls of the second pouch, wherein the first pouch and the second pouch are connected by a common wall, and wherein the first pouch and the second pouch are adapted to be opened independently from each other.

2. Package according to claim 1, wherein the protecting means are consituted of a bandage, a compress, a bandaid or a dressing.

3. Package according to claim 1, wherein the wall or each of the walls of the first pouch whereon is fixed the impregnated support is constructed of a flexible material.

4. Package according to claim 1, wherein at least two pouches are superposed on each other.

5. Package according to claim 1, wherein at least one of the first and second pouches is adapted to ensure the sterility of said contents during storage.

6. Package according to claim 1, wherein the walls of each of the first and second pouches are fixed to each other so as to make it possible to separate said walls by peeling of said walls at the time of opening each said pouch.

7. Package according to claim 1, wherein at least the first pouch comprises an anti-breakup device adapted to prevent, at the time of opening said first pouch, the walls of the first pouch from separating totally from each other.

8. Package according to claim 7, wherein the anti-breakup device of the first pouch is obtained by fixing said impregnated support to the two walls of the first pouch.

9. Package according to claim 8, wherein the anti-breakup device of the first pouch is placed in a staggered position or at an opposite end relative to the anti-breakup device of the second pouch, on the wall common to the two pouches.

10. Package according to claim 7, wherein the anti-breakup device of one of the first pouch is placed in a staggered position or at an opposite end relative to the anti-breakup device of the second pouch, on the wall common to the two pouches.

11. Package according to claim 1, wherein at least one of the first and second pouches comprises an opening facilitator to facilitate its opening.

12. Package according to claim 11, wherein the opening facilitator of one of the first pouch is placed in a staggered position or at an opposite end relative to the opening facilitator of the second pouch, on the wall common to the two pouches.

13. Package according to claim 1, wherein the impregnated support and the protecting means are placed on opposite sides of the common wall.

14. Package according to claim 1, wherein the impregnated support and the protecting means are placed on a same side of the common wall.

15. Package according to claim 1, further comprising at least a third pouch comprising two walls fixed to each other so as to make it possible, at the time of use, to at least partially separate said walls of the third pouch, wherein the third pouch and at least one of the first and second pouches are connected by a common wall, and wherein the third pouch is adapted to be opened independently from the first and second pouches.

16. Package according to claim 15, wherein the first, second, and third pouches are connected by a common wall.

17. Package according to claim 15, wherein the first and second pouches are connected by a common wall, and the second and third pouches are connected by another common wall.

18. Package according to claim 15, wherein the first pouch comprises an anti-breakup device adapted to prevent, at the time of opening said first pouch, the walls of said first pouch from separating totally from each other, the second pouch comprises an anti-breakup device adapted to prevent, at the time of opening said second pouch, the walls of said second pouch from separating totally from each other, and the third pouch comprises an anti-breakup device adapted to prevent, at the time of opening said third pouch, the walls of said third pouch from separating totally from each other.

19. Package according to claim 1, wherein the first pouch comprises an anti-breakup device adapted to prevent, at the time of opening said first pouch, the walls of said first pouch from separating totally from each other, and the second pouch comprises an anti-breakup device adapted to prevent, at the time of opening said second pouch, the walls of said second pouch from separating totally from each other.

* * * * *